United States Patent
McKenna

(10) Patent No.: US 8,577,433 B2
(45) Date of Patent: Nov. 5, 2013

(54) MEDICAL DEVICE ALARM MODELING

(75) Inventor: Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 329 days.

(21) Appl. No.: 12/948,854

(22) Filed: Nov. 18, 2010

(65) Prior Publication Data

US 2011/0118573 A1 May 19, 2011

Related U.S. Application Data

(60) Provisional application No. 61/262,441, filed on Nov. 18, 2009.

(51) Int. Cl.
*A61B 5/1455* (2006.01)

(52) U.S. Cl.
USPC .......................... 600/310; 600/309; 600/300

(58) Field of Classification Search
USPC .............................. 600/309–344, 300; 702/19
See application file for complete search history.

(56) References Cited

U.S. PATENT DOCUMENTS

| | | | |
|---|---|---|---|
| 5,368,026 A | 11/1994 | Swedlow et al. | |
| 5,680,857 A | 10/1997 | Pelikan et al. | |
| 5,807,246 A | 9/1998 | Sakaguchi et al. | |
| 5,920,263 A | 7/1999 | Huttenhoff et al. | |
| 6,398,727 B1 | 6/2002 | Bui et al. | |
| 6,641,533 B2 * | 11/2003 | Causey et al. | 600/300 |
| 6,754,516 B2 | 6/2004 | Mannheimer | |
| 6,792,396 B2 | 9/2004 | Inda et al. | |
| 6,996,427 B2 | 2/2006 | Ali et al. | |
| 7,024,233 B2 | 4/2006 | Ali et al. | |
| 7,123,950 B2 | 10/2006 | Mannheimer | |
| 7,161,484 B2 | 1/2007 | Tsoukalis | |
| 7,268,672 B2 | 9/2007 | King | |
| 7,415,297 B2 | 8/2008 | Al-Ali et al. | |
| 2005/0039742 A1 | 2/2005 | Hickle | |
| 2006/0069319 A1 | 3/2006 | Elhag et al. | |
| 2006/0074321 A1 | 4/2006 | Kouchi | |
| 2006/0195025 A1 | 8/2006 | Al-Ali et al. | |
| 2006/0220881 A1 | 10/2006 | Ali-Ali et al. | |
| 2006/0226992 A1 | 10/2006 | Al-Ali et al. | |

(Continued)

FOREIGN PATENT DOCUMENTS

WO WO2006009830 A2 1/2006
WO WO2006067725 A2 6/2006

OTHER PUBLICATIONS

PCT International Search Report, International Application No. PCT/US2010/057137, Applicant Nellcor Puritan Bennett LLC, Date of Mailing; Feb. 15, 2011, International Filing Date: Nov. 18, 2010.
U.S. Appl. No. 12/409,710, filed Mar. 24, 2009—Batchelder et al.

(Continued)

*Primary Examiner* — Eric Winakur
*Assistant Examiner* — Marjan Fardanesh
(74) *Attorney, Agent, or Firm* — Fletcher Yoder PC

(57) ABSTRACT

Embodiments of the present disclosure relate to patient monitors with alarm modeling features that may be employed to set alarm limits. According to certain embodiments, the patient monitors may include a user interface for setting alarm limits that may be displayed on the patient monitors and/or on an external device, such as a central monitoring station. The user interface may allow a user to vary alarm limit settings and view how the settings change the alarm history for a representative data trend.

20 Claims, 8 Drawing Sheets

(56) References Cited

U.S. PATENT DOCUMENTS

| | | |
|---|---|---|
| 2006/0238358 A1 | 10/2006 | Al-Ali et al. |
| 2007/0032714 A1 | 2/2007 | Mannheimer |
| 2007/0100218 A1 | 5/2007 | Sweitzer et al. |
| 2007/0100219 A1 | 5/2007 | Sweitzer et al. |
| 2007/0109115 A1 | 5/2007 | Kiani et al. |
| 2007/0167693 A1 | 7/2007 | Scholler et al. |
| 2007/0293745 A1 | 12/2007 | McCutcheon et al. |
| 2008/0091092 A1 | 4/2008 | Al-Ali |
| 2008/0183057 A1 | 7/2008 | Taube |
| 2008/0183058 A1 | 7/2008 | Mannheimer |
| 2008/0188733 A1 | 8/2008 | Al-Ali et al. |
| 2008/0194932 A1 | 8/2008 | Ayers et al. |
| 2008/0208011 A1 | 8/2008 | Shuler |
| 2008/0214906 A1 | 9/2008 | Wang et al. |
| 2008/0228052 A1 | 9/2008 | Al-Ali |
| 2008/0300471 A1 | 12/2008 | Al-Ali et al. |
| 2008/0300474 A1 | 12/2008 | Benni et al. |
| 2009/0209839 A1 | 8/2009 | Ochs et al. |
| 2009/0247851 A1 | 10/2009 | Batchelder et al. |
| 2010/0324398 A1* | 12/2010 | Tzyy-Ping .................. 600/365 |

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Belal, Suliman Yousef, et al.; "A fuzzy system for detecting distorted plethysmogram pulses in neonates and paediatric patients," *Physiol. Meas.*, vol. 22, pp. 397-412 (2001).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

\* cited by examiner

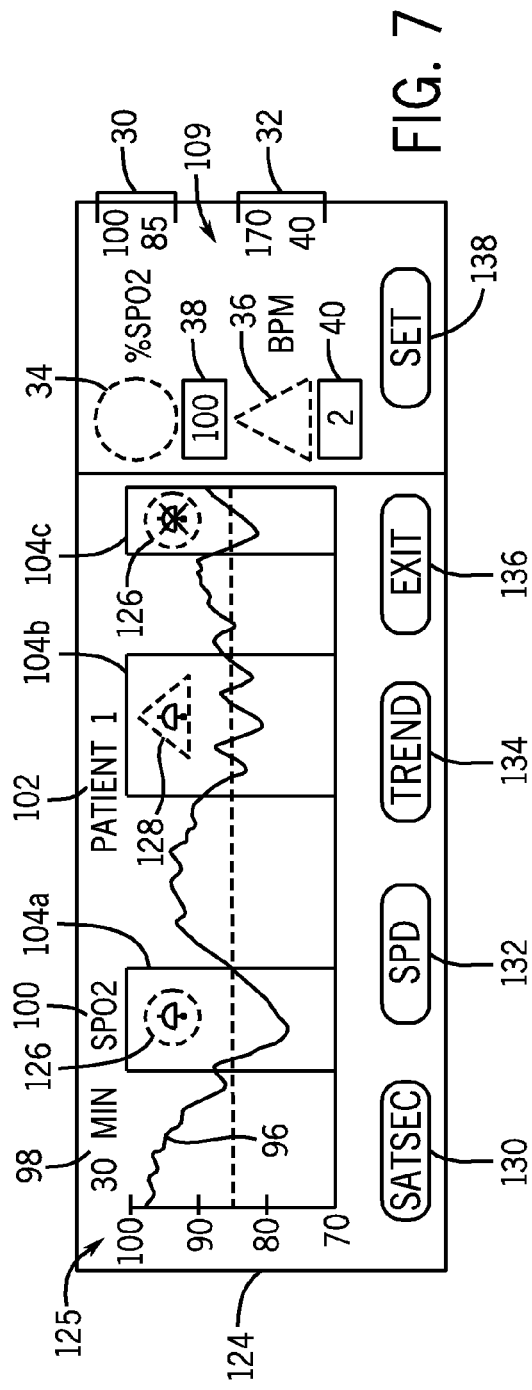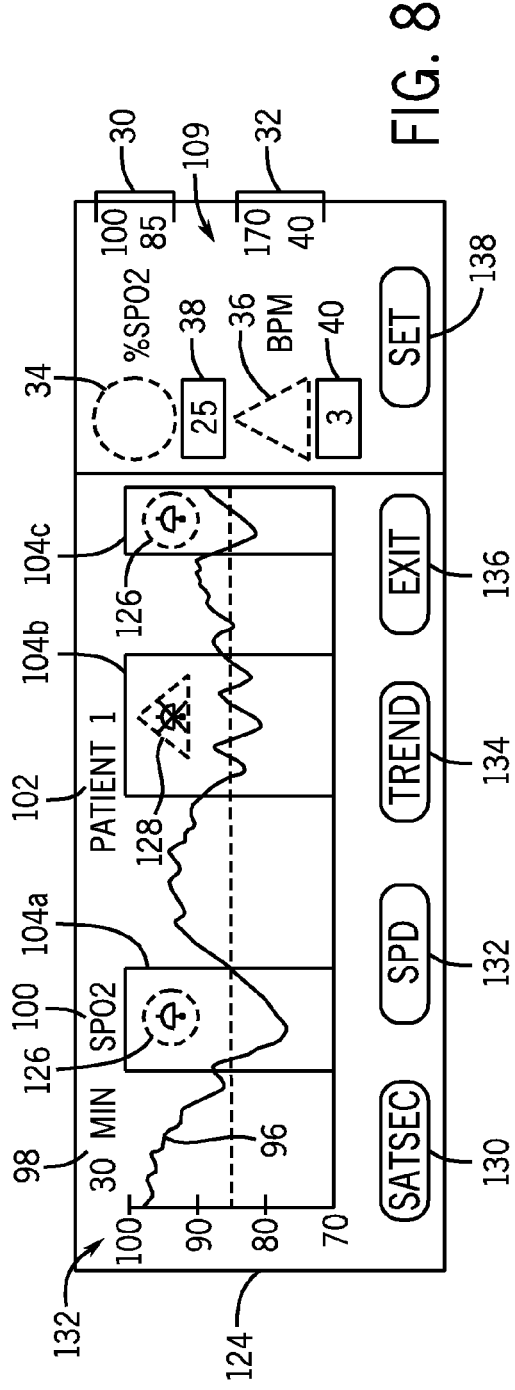

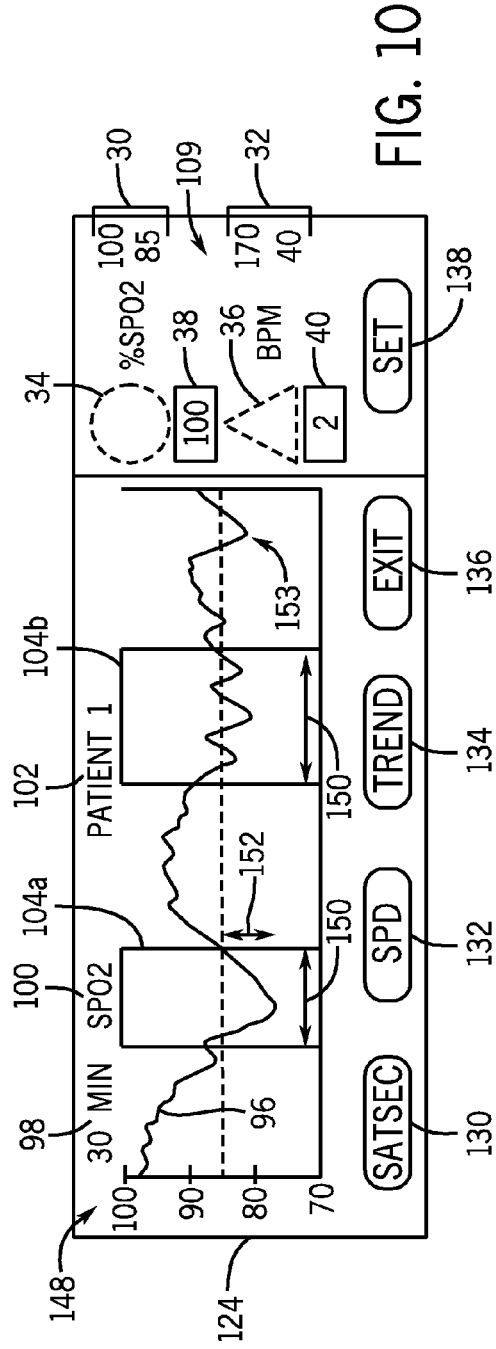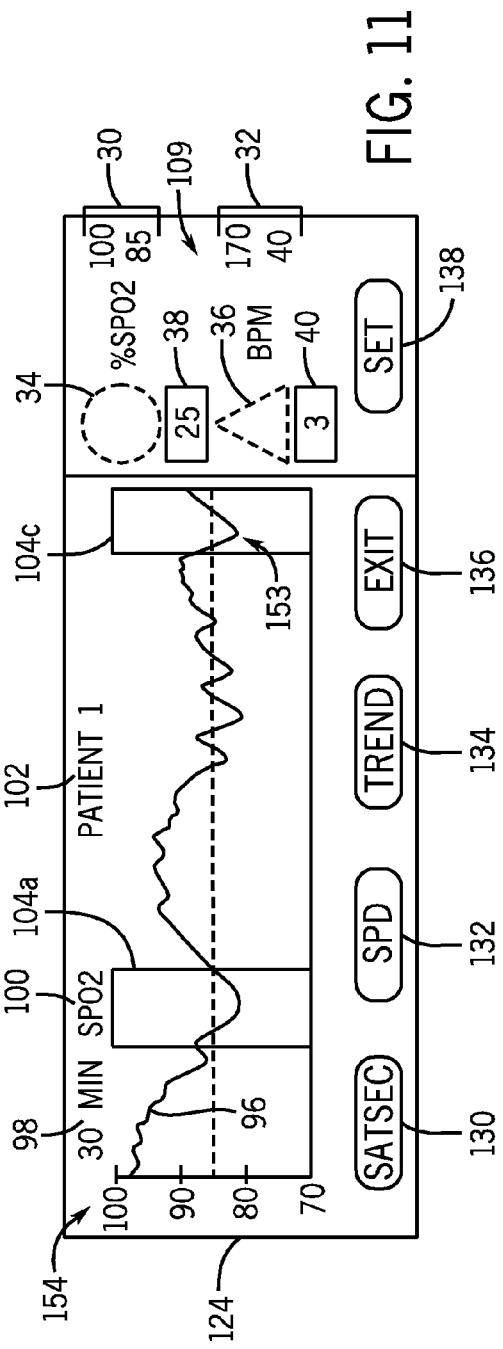

MEDICAL DEVICE ALARM MODELING

RELATED APPLICATION

This application claims the benefit of U.S. Provisional Application No. 61/262,441, filed Nov. 18, 2009, which application is hereby incorporated by reference.

BACKGROUND

The present disclosure relates generally to medical device alarm modeling and, more particularly, to medical device alarm modeling features for setting alarm limits.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Patient monitors include medical devices that facilitate measurement and observation of patient physiological data. For example, pulse oximeters are a type of patient monitor. A typical patient monitor cooperates with a sensor to detect and display a patient's vital signs (e.g., temperature, pulse rate, respiratory rate) and/or other physiological measurements (e.g., water content of tissue, blood oxygen level) for observation by a user (e.g., clinician). For example, pulse oximeters are generally utilized with related sensors to detect and monitor a patient's functional oxygen saturation of arterial hemoglobin (i.e., $SpO_2$) and pulse rate. Other types of patient monitors, such as blood pressure monitors, may be utilized to detect and monitor other physiological parameters. Further, the patient monitors may be incorporated into other types of medical devices, such as mechanical ventilators and anesthesia machines, among others.

A patient monitor may be designed to alert a caregiver when certain physiological conditions are recognized. For example, a pulse oximeter may produce a visual and/or audible alarm when a patient's oxygen saturation exceeds a predetermined threshold. The predetermined alarm thresholds may be set by the patient monitor, and, in certain circumstances, may be customizable by a user. Further, in addition to alarm thresholds, a patient monitor may be designed to provide more complex alarm features. For example, a patient monitor may be designed to minimize clinically insignificant alarms and/or to recognize patterns in physiological data. The alarms may be based on multiple variables and may interact with other alarms, which may complicate the setting of alarm limits by a caregiver.

BRIEF DESCRIPTION OF THE DRAWINGS

Advantages of the disclosed techniques may become apparent upon reading the following detailed description and upon reference to the drawings in which:

FIG. 7 is a representation of a screen displaying a representative plethysmographic waveform with indicators that may be manipulated through a touch screen;

FIG. 8 is a representation of a screen displaying the representative plethysmographic waveform of FIG. 7 after the alarm limits have been adjusted;

FIG. 10 is a representation of a screen displaying a representative plethysmographic waveform that may be manipulated to set alarm thresholds; and FIG. 11 is a representation of a screen displaying the representative plethysmographic waveform of FIG. 10 after manipulation of the representative plethysmographic waveform.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to patient monitors with alarm modeling features that may be employed to set alarm limits. According to certain embodiments, the patient monitors may include a user interface for setting alarm limits that may be displayed on the patient monitors and/or on an external device, such as a central monitoring station. The user interface may allow a user to vary alarm limit settings and view how the settings change the alarm history for a representative data trend. For example, a graphical representation, such as a representative plethysmographic ("pleth") waveform, may be displayed on the user interface along with indicators identifying alarm conditions on the representative pleth waveform. The representative pleth waveform may display sample data or may display actual patient data.

As a user adjusts alarm limit settings, the alarm modeling feature may analyze the physiological data corresponding to the representative pleth waveform to identify alarm conditions for the adjust alarm limit settings. The alarm modeling feature may then update the indicators on the representative pleth waveform to reflect the newly determined alarm conditions. Accordingly, a user may be able to see how the changed alarm settings may change alarm frequency and/or duration for actual or sample data. In certain embodiments, the indicators may identify potential alarm conditions as well as actual alarm conditions that may produce an alarm under the adjusted alarm limit settings. For example, the indicators may identify sections of the representative plethysmographic waveform that may not produce an alarm under the current settings, but may produce an alarm if the alarm settings were adjusted.

Figure 1:
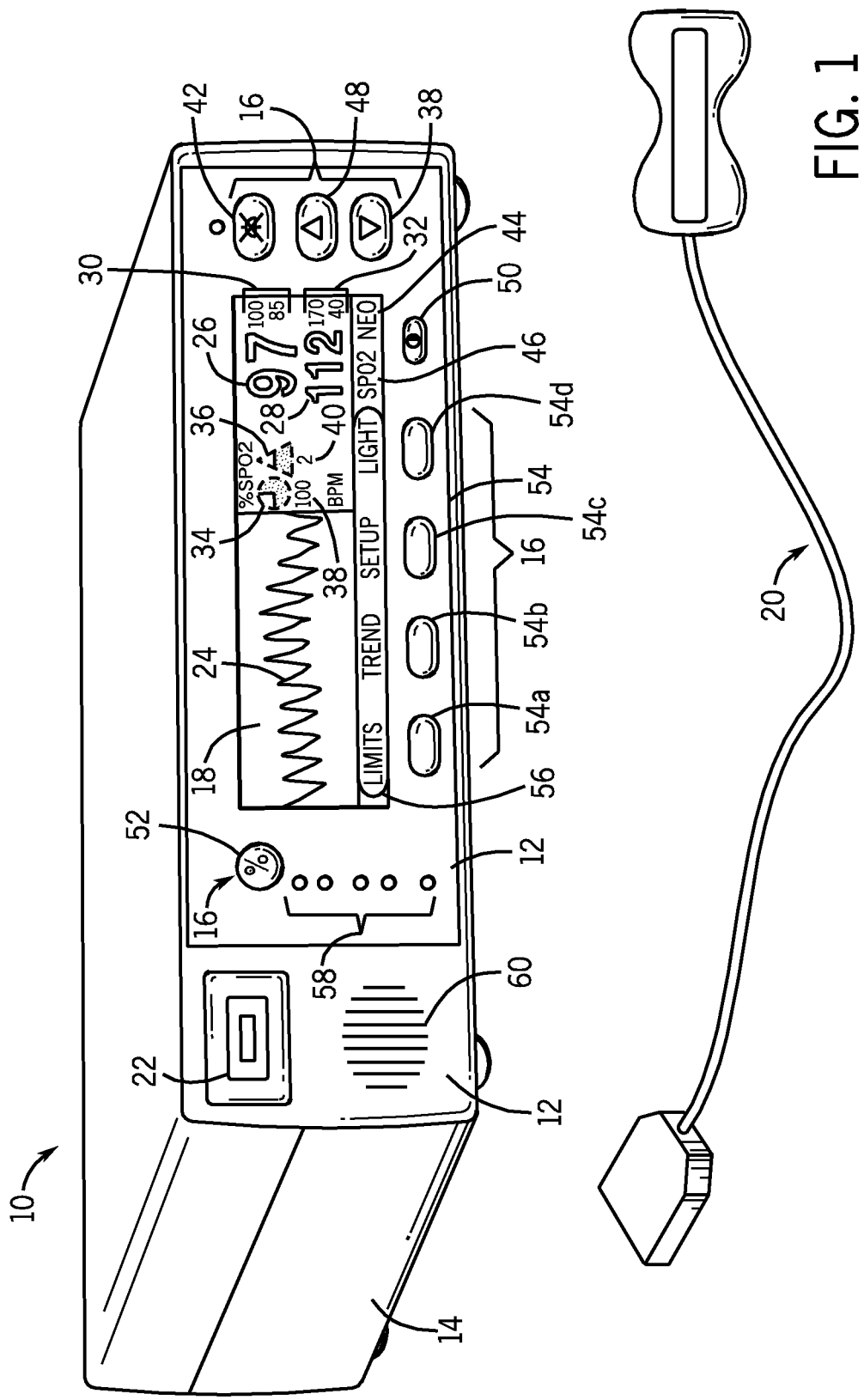
FIG. 1 is a perspective view of an embodiment of a patient monitor that may employ an alarm modeling feature.

FIG. 1 is a perspective view of an embodiment of a patient monitor 10 that may employ an alarm limit user interface. For example, the patient monitor 10 may be a pulse oximeter, such as those available from Nellcor Puritan Bennett LLC of Boulder, Colo. As shown, the patient monitor 10 is a pulse oximeter designed to detect and monitor blood oxygen saturation levels, pulse rate, and so forth. However, in other embodiments, the alarm modeling features may be employed in other types of patient monitors, such as vital signs monitors, critical care monitors, obstetrical care monitors, or blood pressure monitors, among others. Further, the patient monitor 10 may be part of a therapeutic medical device, such as a mechanical ventilator, or anesthesia machine, among others.

The patient monitor 10 includes a front panel 12 coupled to a body 14 of the patient monitor 10. The front panel 12 may include several selectable inputs 16 that may be actuated by a caretaker to operate the patient monitor 10. For example, the selectable inputs 16 may include buttons that may be pressed to change information shown on a display 18. In other embodiments, the size, shape, locations, and/or labels for the selectable inputs 16 may vary. For example, the selectable inputs 16 may be arranged on different parts of the patient monitor 10 and/or located on an external device. In another example, some or all of the selectable inputs 16 may be graphical elements selected through a touch screen of the patient monitor 10 or through a touch screen of an external device. Further, some or all of the selectable inputs 16 may include different types of inputs, such as knobs, buttons, slide bars, joysticks, and/or wheels, among others.

In certain embodiments, the display 18 may include a cathode ray tube or liquid crystal display. Moreover, the display 18 may include an optional touch screen. In general, the display 18 may show processed physiological data and/or other data received through a medical device interface, such as a cable connection port 22, from a patient sensor 20, or other suitable medical device, such as a therapy device. As shown, the medical device interface 22 includes a cable connection port. However, in other embodiments, the medical device interface 22 may any suitable type of interface for connecting to a medical device. For example, in certain embodiments, the medical device interface 22 may include a wireless interface.

According to certain embodiments, the display 18 may be used to display a plethysmographic ("pleth") waveform 24, an oxygen saturation 26, and/or a pulse rate 28. The oxygen saturation 26 may be a functional arterial hemoglobin oxygen saturation measurement displayed as units of percentage $SpO_2$. The pulse rate 28 may indicate a patient's pulse rate in beats per minute. The display 18 also may be used to show topic-specific screens related to the physiological data, such as a "blip" display that includes pulse amplitude blips, a real-time trend display, and a monitoring mode display that is easy to read from a distance. Moreover, the display 18 may be used to display user interface options, such as a setup and/or configuration screen for adjusting parameters such as alarm volume, display scales, and alarm limits, among others.

In addition to displaying physiological information, the patient monitor 10 also may display information related to alarms and monitor settings on the display 18. For example, the display 18 may display alarm limits 30 and 32 for the oxygen saturation 26 and the pulse rate 28. If an alarm limit 30 or 32 is exceeded, the patient monitor 10 may produce a visible and/or audible alarm. The display 18 also may display indicators 34 and 36 for alarm management features. For example, in some embodiments, the patient monitor 10 may employ SatSeconds™ by Nellcor™ to detect alarms and manage nuisance alarms. SatSeconds™ may include activation of an alarm based on limits that may include the integral of time and depth of a desaturation event and may include an indicator 34 that may serve to inform the caregiver that an $SpO_2$ reading has been detected outside of the limit settings.

According to certain embodiments, the SatSeconds™ alarm management feature may analyze $SpO_2$ excursions outside of the alarm limits 30 to differentiate between clinically significant desaturations and minor transient events. For example, SatSeconds™ may enable oxygen saturation alarms only when a SatSeconds™ value, represented by a combination of the magnitude and time of the oxygen saturation excursion, exceeds a certain threshold. In general, the SatSeconds™ value may be the product of the magnitude and duration of an oxygen desaturation event. Accordingly, shallow and/or short desaturation readings that may be measurement noise (e.g., that otherwise may trigger nuisance alarms) may not produce an alarm, allowing caregivers to put brief desaturation events into context with their depth and to put shallow desaturations into context with their duration. In summary, the SatSeconds™ alarm management feature may filter out nuisance alarms to produce a higher ratio of alarms when a clinically significant excursion occurs, as determine by the SatSeconds™ setting.

A label 38 may be displayed adjacent to the indicator 34 to display the current SatSeconds™ setting. For example, the SatSeconds™ value may be set to 10, 25, 50 or 100 SatSeconds™, with 100 SatSeconds™ representing the highest threshold for producing an alarm and 10 SatSeconds™ representing the lowest threshold for producing alarms. As shown, the SatSeconds™ value is set to 100, and, therefore, only events that equal or surpass the 100 SatSeconds™ limit may trigger an oxygen saturation alarm. As the SatSeconds™ value increases, the SatSeconds™ indicator 34 may fill up. When the SatSeconds™ indicator 34 is full, the SatSeconds™ value may have been reached or exceeded, and the patient monitor 10 may produce an alarm.

In certain embodiments, the patient monitor 10 also may employ an OxiMax SPD™ alert by Nellcor™ to detect patterns of desaturation that are indicative of repetitive reductions in airflow. For example, the OxiMax SPD™ alarm management feature may analyze oxygen saturation trend data to determine if ventilatory instability is present. The Saturation Pattern Detection ("SPD") indicator 36 may provide information to a user related to the occurrence, frequency, and/or magnitude of the patterns detected. As patterns are detected, an index value may increase until the alarm threshold is reached, resulting in an alarm. For example, the index value may be a scoring index, such as a Saturation Pattern Detection index (SPDi), which may represent the magnitude and variability of ventilator variations detected by patterns in the oxygen saturation values. In certain embodiments, the SPDi may be calculated using features such as the magnitude of the $SpO_2$ pattern, the variability in the $SpO_2$ peaks, and the variability in the nadir. In these embodiments, the graphical indicator 36 may gradually fill as the SPDi index increases.

The OxiMax SPD™ alert may include several tolerance settings that may be selected by a user. For example, the tolerance setting may be set to low (level 1), medium (level 2), or high (level 3). Under the high tolerance setting only the most severe patterns may produce an SPD alarm while under the low tolerance setting, even the least severe patterns may trigger an SPD alarm. A label 40 may be displayed near the indicator 36 to represent the selected tolerance setting. As shown, the tolerance setting is currently set to medium, as indicated by the number "2," indicating that mid severity level and above patterns may trigger an SPD alarm. As the SPDi value increases, the SPD indicator 36 may fill up. When the SPD™ indicator 36 is full, the tolerance setting may have been reached or exceeded, and the patient monitor 10 may produce an alarm. Moreover, in certain embodiments, an intermediate alarm may be triggered, for example, when the indicator 36 reaches a certain fill level, such as 10%, 25%, or 50%.

When an alarm is triggered, one of the selectable inputs 16, such as an alarm silence button 42, may be actuated to silence the alarm and display an alarm silence indicator (not shown), such as a slash and a timer, on the display 18. The display 18 also may show mode setting information describing a specific mode to which the alarm limits are set. For example, the display 18 may show an indicator 44 that informs a caretaker that neonatal alarm limits are currently applied rather than adult alarm limits. In another example, the display 18 may show an indicator 46 that informs a caretaker that the patient monitor 10 is operating in a fast alarm response mode rather than a normal alarm mode.

In general, the selectable inputs 16 may be used to control operating functions of the patient monitor 10. The selectable inputs 16 may include fixed function keys, such as the alarm silence button 42, arrow keys 48, a contrast selection key 50, and a power key 52. For example, the arrow keys 48 may be actuated to adjust alarm limits and/or to vary the physiological information shown on the display 18. In another example, the contrast selection key 50 may be actuated to adjust the contrast of the display 18. Further, the fixed function keys may be programmed to control multiple functions or to operate in different manners based upon various factors, such as the duration the key is pressed, the simultaneous activation of other keys, and so forth. For example, an arrow key 48 may be configured to scroll upwards or downwards more rapidly based upon how long the respective key is held down.

The monitor 10 also may include programmable function keys ("soft keys") 54, and associated soft key icons in the soft key menu 56. Each of the four soft keys 54a, 54b, 54c, and 54d may be pressed to select a corresponding function indicated by the respective soft key icon. For example, the soft key 54a may be pressed to display "LIMITS" information, while the soft key 54b may be pressed to display "TREND" information. In certain embodiments, the soft keys 54 may be programmed to display operating information such as alarm limits, historic trends, setup menus, and alarm volume settings, among others. Moreover, a caregiver may actuate the soft keys 54 to display various operating menus, and then may use the arrow keys 48 to adjust operating parameters. Further, in certain embodiments, a caregiver may navigate through the user interface of the patient monitor 10 using the soft keys 54 and the fixed function keys (e.g., 42 and 48) to adjust alarm limit settings. For example, a caretaker may select the soft key 54a to access the graphical user interface for modeling alarms as described below with respect to FIGS. 4-10.

In addition to the selectable inputs 16, the front panel 12 may include various indicators 58 (e.g., indicator lights and display screen graphics) that facilitate operation of the monitor 10 and observation of a patient's physiological metrics (e.g., pulse rate). Some of the indicators 58 are specifically provided to facilitate monitoring of a patient's physiological parameters. For example, the indicators 58 may include representations of the most recently measured values for $SpO_2$, pulse rate, and pulse amplitude. Other indicators 58 may be specifically provided to facilitate operation of the monitor 10. For example, the indicators 58 may include an A/C power indicator, a low battery indicator, an alarm silence indicator, a mode indicator, and so forth. The front panel 12 also includes a speaker 60 for emitting audible indications (e.g., alarms). In other embodiments, the indicators 58 and/or the speaker 60 may be located on other locations of the patient monitor 10 or on an external device.

Figure 2:
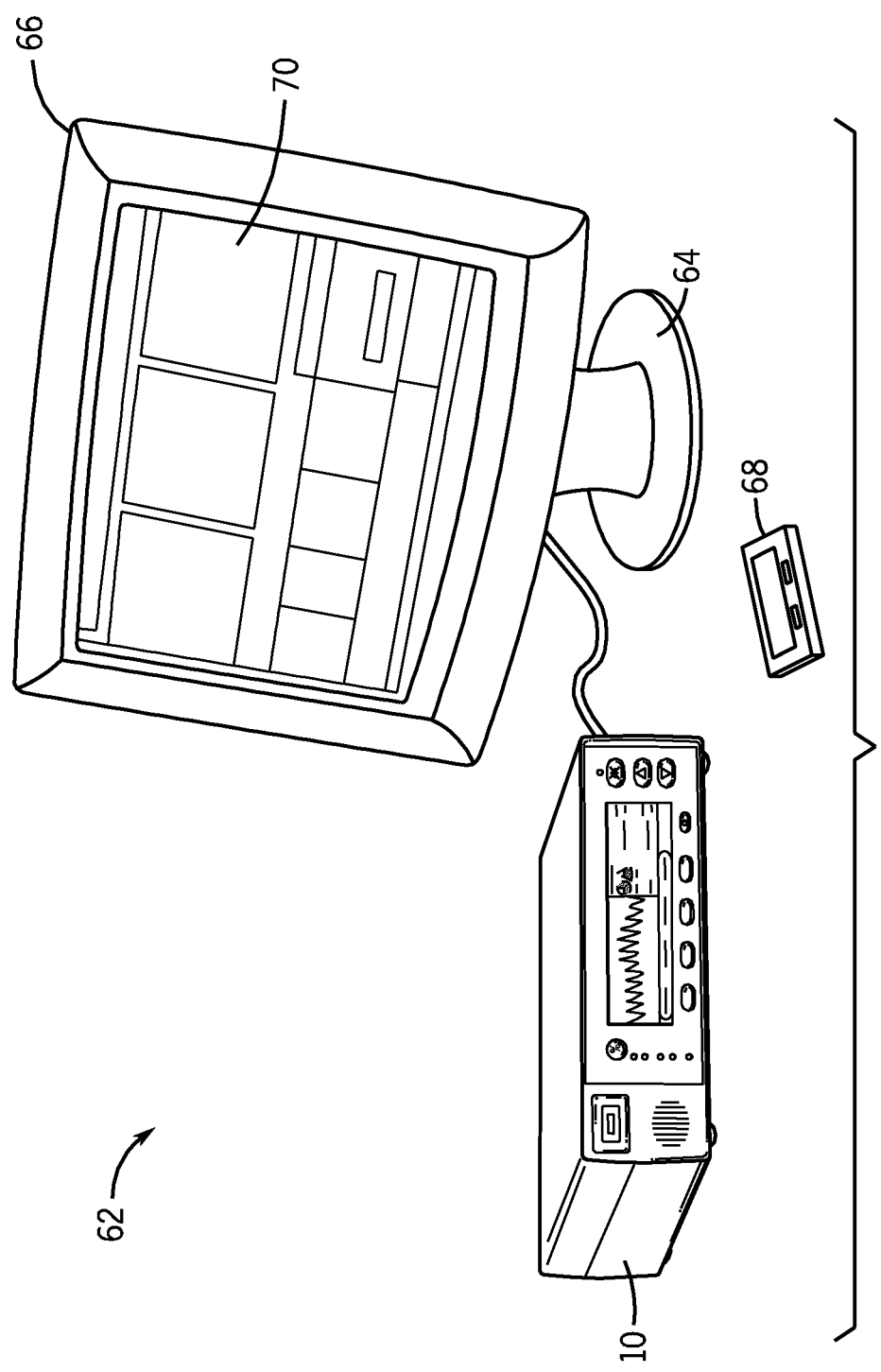
FIG. 2 is a perspective view of an embodiment of a patient monitoring system that includes the patient monitor of FIG. 1.

FIG. 2 depicts a monitoring system 62 that may employ the patient monitor 10. The monitoring system 62 includes a central station 64 that may be connected to one or more patient monitors 10 by a hardwired or wireless communication link. According to certain embodiments, the central station 64 may be a Nellcor Oxinet® III Central Station, available from Nellcor™. The central station 64 may include a display 66 that displays physiological data from the connected patient monitors 10. The central station 64 may allow a caretaker to monitor the physiological data from several patients in a single location. Further, the central station 64 may produce corresponding alarms when a patient monitor 10 alarms. The monitoring system 62 also may include one or more pagers 68 that individual caretakers may carry with them to receive alarms from the central station 64.

The central station 64 may include one or more input devices, such as a touch screen 70, that allow a user to control operations of the monitoring system 62. In other embodiments, the input devices may vary. For example, the input devices may include a keyboard, remote control, or mouse, among others. Through the input devices 70, a user may adjust alarm settings for the connected patient monitors 10. A user also may manipulate the input devices 70 to change other setup options for the patient monitors 10 and to view information about the physiological data. For example, a user may manipulate the touch screen 70 to view trend data, alarm limits, or current settings for a patient monitor 10 that is part of the monitoring system 62.

Figure 3:
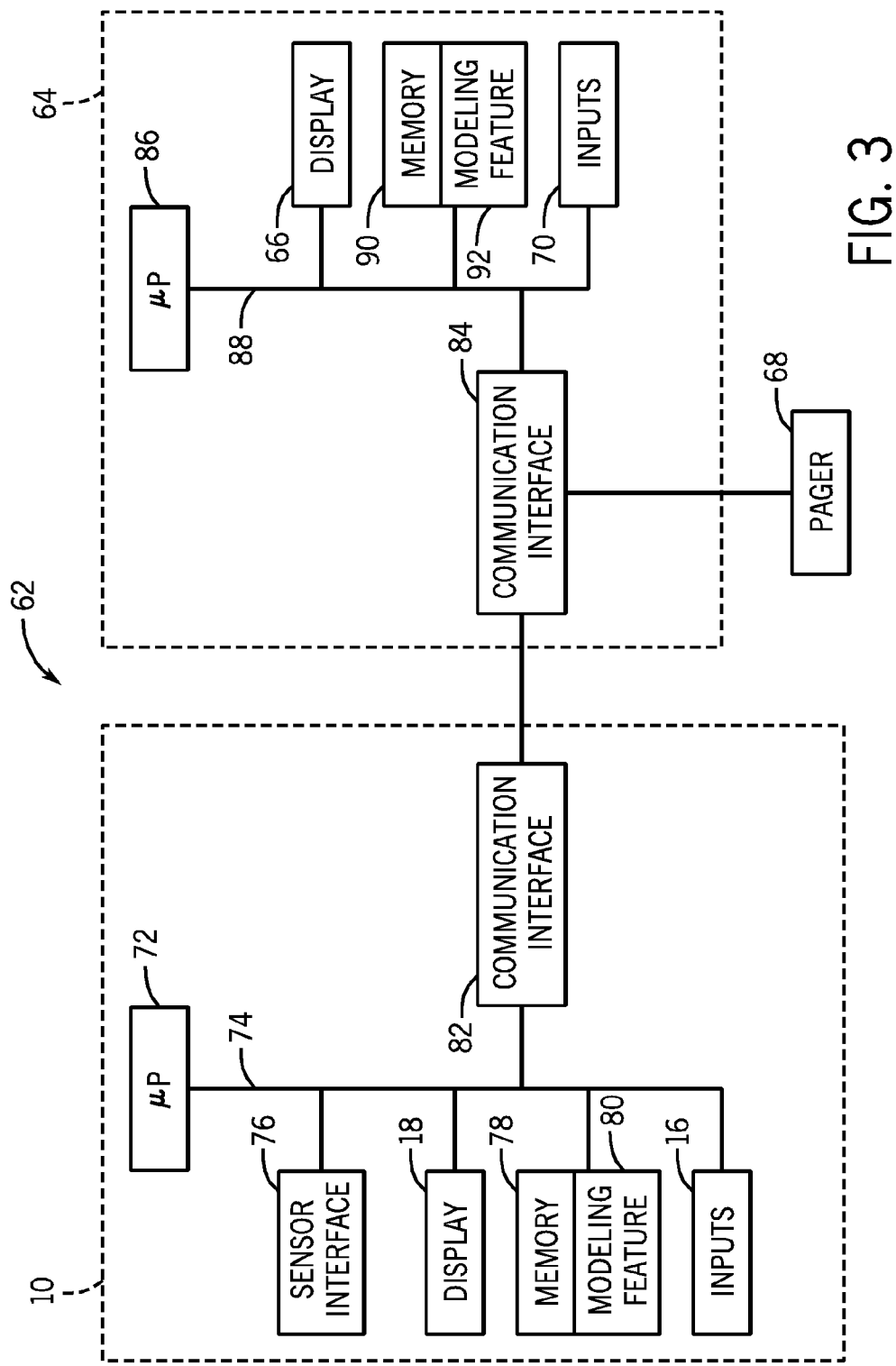
FIG. 3 is a block diagram of an embodiment of the patient monitoring system of FIG. 2.

FIG. 3 is a block diagram of the embodiment of the monitoring system 62 shown in FIG. 1. The patient monitor 10 generally includes a microprocessor 72 connected to an internal bus 74. A sensor interface 76 may be connected to the bus 82 and may allow the patient monitor 10 to communicate with and receive physiological data from the sensor 20 (FIG. 1). In certain embodiments, the sensor interface 76 may include components, such as a decoder for decoding signals from the sensor, algorithms or lookup tables for identifying physiological parameters, drive circuits, and signal-processing equipment, such as filters, analog to digital converters, amplifiers, queued serial modules, and time processing units, among others.

In general, the sensor interface 76 may be designed to receive input from the sensor 20 and transmit signals to the microprocessor 80 in a form that the microprocessor may use to calculate and/or to determine physiological parameters, for example, based on algorithms or look-up tables stored in a memory 78. In certain embodiments, the microprocessor 80 may use the information from the sensor interface 76 to determine physiological parameters, such as $SpO_2$, pulse rate, respiratory effect, and so forth. The physiological parameters may then be displayed on the display 18. For example, as shown in FIG. 1, the physiological parameters, such as the pleth waveform 24, the pulse rate 28, and the oxygen saturation 26, may be shown on the display 18.

The microprocessor 80 may analyze the physiological parameters and may produce alarms when the physiological parameters exceed alarm limits stored within the memory 78. In addition to the alarm limits, the memory 78 may store operating parameters for alarm management features, such as SatSeconds™ and/or Oximax SPD™ alert. The memory 78 may include volatile memory, such as random access memory (RAM) and/or non-volatile memory, such as read-only memory (ROM), and the like.

A user may adjust the alarm limits and settings through an alarm modeling feature 80 stored within the memory 78. The alarm modeling feature 80 may include a graphical user interface that enables a user to change the alarm settings and view how the changed settings affect alarm conditions for a graphical representation of representative physiological data. The graphical representation is generally described herein in the context of a representative pleth waveform. However, in other embodiments, the graphical representation may include any suitable type of graphical representation of patient physiological data.

In general, the graphical representation may be designed to simulate patient physiological data. For example, the graphical representation may include a representative pleth waveform that may be based on a sample waveform stored within the memory 78 or may be based on a waveform generated using a patient's physiological data. For example, as the patient monitor 10 collects physiological data for a patient, the patient monitor 10 may generate historical trend information that includes a pleth waveform. In certain embodiments, the historical trend information may be stored within the memory 78 and used as the representative pleth waveform. In other embodiments, one or more representative pleth waveforms may be based on sample physiological data and stored within the memory 78. A representative pleth waveform may be selected by the alarm modeling feature 80 based on the current alarm settings. For example, certain representative pleth waveforms may be used to model alarms when the oxygen saturation limits are set within a specified range. In another example, certain representative pleth waveforms may be used to model alarms when alarm management features, such as SatSeconds™ and the OxiMax SPD™ alert, are enabled.

The alarm modeling feature 80 may include software elements, such as computer code, that operate in conjunction with the microprocessor 72 to display alarm conditions on the display 18 that correspond to the representative pleth waveform. For example, the representative pleth waveform may be shown on the display with indicators that identify where alarm conditions occurred on parts of the pleth waveform. As a user changes the alarm limit settings, the alarm modeling feature 80 may determine the new alarm conditions corresponding to the changed settings and may display the new alarm conditions on the display with the representative pleth waveform. Accordingly, a user may be able to see how the changed alarm settings affect the alarm frequency and/or duration.

In certain embodiments, the representative pleth waveform may be shown on the central station 64. The patient monitor 10 and the central station 64 may include corresponding communication interfaces 82 and 84 that enable communication between the patient monitor 10 and the central station 64. For example, the communication interfaces 82 and 84 may be network connections enabling wired or wireless network communications. Information from the patient monitor 10 may be transmitted to a microprocessor 86 within the central station 64 via an internal bus 88. For example, graphical user interface screens for the alarm modeling feature 80 may be transmitted through the communication interfaces 82 and 84 and the bus 88 to be shown on the display 66 of the central station 64. A user may then change alarm limit settings for the patient monitor 10 through the inputs 70 (e.g., a touch screen) and display 66 of the central station 64.

In certain embodiments, information for changing the alarm limits may be stored within a memory 90 of the central station 64. The memory 80 may include volatile memory, such as random access memory (RAM) and/or non-volatile memory, such as read-only memory (ROM), and the like. For example, the memory 80 may store an alarm modeling feature 92 that corresponds to the alarm modeling feature 80 of the patient monitor 10. In certain embodiments, only one of the alarm modeling features 80 or 92 may be included within the monitoring system 62. However, in other embodiments, the monitoring system 62 may include both alarm modeling features 92 and 80. For example, the alarm modeling feature 92 may include a graphical user interface for displaying alarm limits for multiple patient monitors 10 and may be used in conjunction with the alarm modeling feature 80 of the patient monitor 10. In another example, the alarm modeling feature 92 of the central station 64 may include a graphical user interface for changing alarm settings of multiple patient monitors 10 coupled to the central station 64.

The communication interface 84 may receive alarms from the patient monitor 10 and may produce alarms on the display 66. Further, although not shown, the central station 64 may include a speaker for producing audible alarms. The communication interface 84 also may transmit alarms to one or more pagers 68 carried by caregivers.

Figure 4:
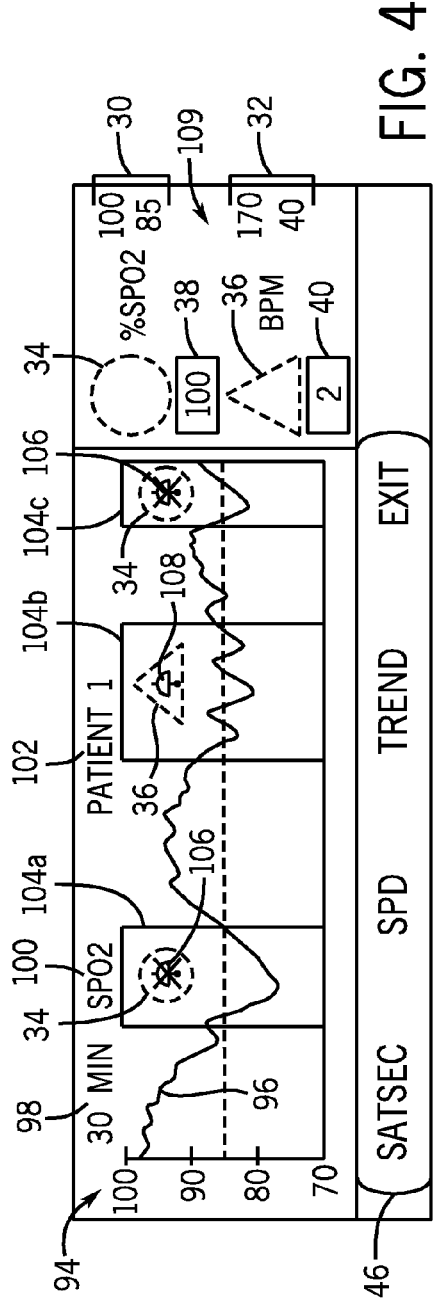
FIG. 4 is a representation of a screen displaying a representative plethysmographic ("pleth") waveform that may be employed to set alarms thresholds for a patient monitor.

FIG. 4 shows a screen 94 of the alarm modeling feature 80 that may be used to set alarm limits. The screen 94 may be shown on the display 18 of the patient monitor 10 and/or on the display 66 of the central station 64. The screen 94 includes a representative pleth waveform 96 that may be used to illustrate changes to the alarm limits. As noted above with respect to FIG. 3, the representative pleth waveform 96 may be a sample waveform stored within the memory 78 (FIG. 3) of the patient monitor 10. However, as shown, the representative pleth waveform 96 is a historical trend for a patient monitored by the patient monitor 10. A label 98 identifies the length of the trend shown, in this case, 30 minutes. The screen 94 also includes a label 100 indicates the type of physiological data shown by the representative pleth waveform 96, in this case, oxygen saturation. However, in other embodiments, the representative pleth waveform 96 may be based on other types of physiological data, such as a pulse rate, among others.

A label 102 may identify the source of the representative pleth waveform 96. For example, the label 102 may identify whether the representative pleth waveform 96 corresponds to a sample waveform stored within the memory 78 or to a historical trend of patient data. The label 102 may further identify the type of sample waveform or the patient on which the representative pleth waveform is based. The label 102 may be particularly helpful when the screen 94 is shown on the display 66 of the central station 64 to identify which patient the waveform corresponds to when several patients are monitored by the central station 64.

Sections 104 of the representative waveform 96 may be highlighted to identify potential alarm conditions on the representative waveform 96. For example, the highlighting may identify excursions outside of the alarm limits 30 for oxygen saturation, or alarm conditions identified by alarm management features, such as the SatSeconds™ or the OxiMax SPD™ alerts. Indicators 34 and 36 may be shown within the sections 104 to specify the type of alarm condition identified for the sections 104. For example, the SatSeconds™ indicator 34 may be shown within the highlighted sections 104a and 104c to indicate that the alarm condition has been identified by the SatSeconds™ alarm management feature. In another example, the OxiMax SPD™ indicator 36 may be shown within the highlighted section 104b to indicate that the alarm condition has been identified by the OxiMax SPD™ alert feature.

Graphical elements 106 and 108 may be shown within or near the indicators 34 and 36 to indicate whether an alarm would occur based on the currently set alarm limits. The current alarm limits may be shown within a portion 109 of the screen 94. For example, the label 38 indicates that the SatSeconds™ threshold is set to the SatSeconds™ value of 100, and a label 40 indicates that the OxiMax SPD™ threshold is set to the middle level. Further, the alarm limits 30 and 32 are displayed for the oxygen saturation and the pulse rate.

Specifically, the graphical element 106 may indicate that an alarm would not occur, while the graphical element 108 may indicate than an alarm would occur. For example, the highlighted section 104a includes the indicator 106 indicating that an alarm would not occur based on the current SatSeconds™ alarm threshold. However, the SatSeconds™ indicator 34 remains shown within the section 104a to indicate that this portion of the representative pleth waveform 96 may produce an alarm is another SatSeconds™ threshold is selected. The highlighted section 104b includes the graphical element 108 indicating that an alarm would occur under the current OxiMax SPD™ setting. The highlighted section 104c includes the graphical element 106 indicating that under the current SatSeconds™ setting the alarm threshold has not been exceeded.

While viewing the representative waveform 96, a user may select soft keys 54 (FIG. 1) corresponding to the indicators 46 shown in the soft key menu 46. For example, a user may select the soft key 54a (FIG. 1) corresponding to the "SATSEC" label to display a menu for adjusting the SatSeconds™ value, for example, from 100 to 25 SatSeconds™. In another example, a user may select the soft key 54b (FIG. 1) corresponding to the "SPD" label to display a screen for adjusting the SPD threshold level. A user also may customize the representative waveform 96 shown on the screen 94. For example, a user may select the soft key 54c (FIG. 1) corresponding to the "TREND" label to change the representative pleth waveform 96 shown on the screen 94. In certain embodiments, a user may select from several representative pleth waveforms 96 stored within the memory 78 (FIG. 3). Moreover, a user may use the trend menu to select a historical trend waveform for another patient or to change the timeframe of the historical trend waveform. Further, a user may select the soft key 54d (FIG. 1) corresponding to the "EXIT" label to exit the alarm setting menu. In other embodiments, other types of selectable inputs 16 (FIG. 1) and/or input devices, such as keyboards, touch screens, or the like, may be employed to vary the alarm settings and/or the view of the representative pleth waveform 96.

Figure 5:
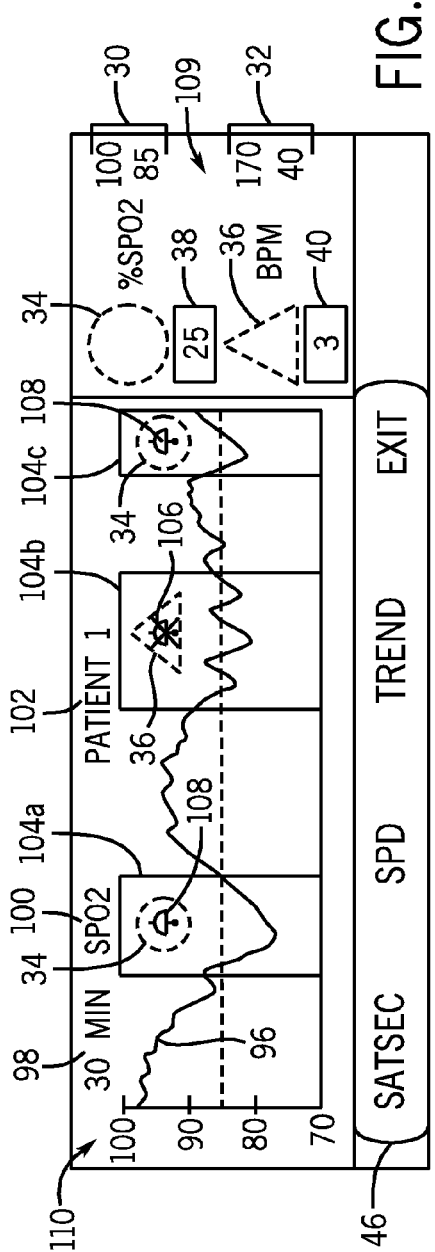
FIG. 5 is a representation of a screen displaying the representative plethysmographic waveform of FIG. 4 after the alarm limits have been adjusted.

As a user changes the alarm limits, the alarm modeling feature 80 may calculate new alarm conditions and display indicators 106 and 108 corresponding to these new alarm conditions. FIG. 5 illustrates a screen 110 that depicts the newly determined alarm conditions on the representative pleth waveform 96. For example, a user has adjusted the SatSeconds™ value from 100 to 25 as shown by the label 30. In general, the user has decreased the SatSeconds™ threshold value, which may result in more alarms being produced by the SatSeconds™ alarm feature. A user also has adjusted the SPD threshold from a mid level indicated by the number 2 to a high level indicated by the number 3, shown by the label 40. The higher threshold may result in fewer alarms being produced by the OxiMax SPD™ alert feature.

The differences in the alarm conditions may be seen by comparing the indicators 106 and 108 shown in FIGS. 4 and 5. Specifically, under the new alarm settings, the highlighted sections 104a and 104e, which did not produce alarms under the previous settings shown in FIG. 4, may now produce alarms as shown in FIG. 5. However, the middle section 104b, which previously produced an alarm based on the OxiMax SPD™ alert feature, may no longer produce an alarm as shown by the graphical element 106. In general, the representative waveform 96 may allow a caregiver to see how changes to the alarm settings may affect the alarm frequency and duration. The modeling of alarm conditions using the representative waveform 96 may be particularly useful when adjusting more complicated alarm management features such as the SatSeconds™ alarm management feature and the OxiMax SPD™ alert feature.

Figure 6:
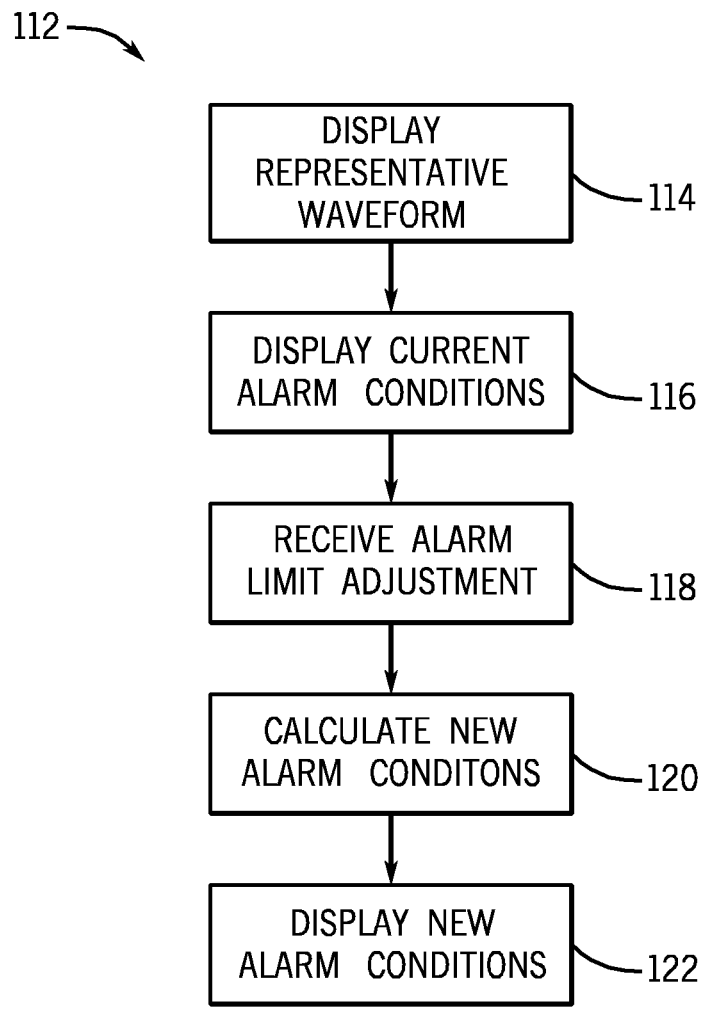
FIG. 6 is a flowchart depicting an embodiment of a method for modeling alarms.

FIG. 6 depicts an embodiment of a method 112 for modeling alarm conditions based on the changes to the alarm limit settings. In general, the method 112 may begin by displaying (block 114) a representative pleth waveform. For example, the patient monitor 10 may show the representative pleth waveform 96 as shown in FIGS. 4 and 5 on the display 18 of the patient monitor 10 and/or on the display 66 of the central station 64. The patient monitor 10 may then display (block 116) the current alarm conditions. For example, as shown in FIGS. 4 and 5, the potential alarm conditions may be identified by the highlighted sections 104, and the indicators 106 and 108 may specify whether an alarm may be produced for each highlighted section 104.

A patient monitor 10 may then receive (block 116) an alarm limit adjustment. For example, a user may use the selectable inputs 16 to adjust the oxygen saturation limits 30, the pulse rate limits 32, the SatSeconds™ value 38, or the SPD threshold 40, among others. Upon receiving (block 118) the alarm limit adjustment, the patient monitor 10 may then calculate (block 120) the new alarm conditions. For example, the processor 72 of the patient monitor 10 may compare the physiological data corresponding to the representative pleth waveform 96 to the adjusted alarm limits to determine whether alarm conditions have been met. In certain embodiments, combinations of hardware elements (e.g., circuitry) and software elements (e.g., machine readable code) may be employed to calculate the new alarm conditions.

After determining the new alarm conditions, the patient monitor 10 may then display (block 122) the new alarm conditions. For example, the patient monitor 10 may display the screen 110 showing an updated display of the indicators 106 and 108 on sections 104 the representative waveform 96. In certain embodiments, the user may then apply the adjusted alarm limits to one or more patient monitors 10. For example, a user may apply the new alarm limits to a single patient monitor 10 or to some or all of the patient monitors connected to the central monitoring station 64.

FIGS. 7 and 8, depict embodiments where a user may adjust the alarm settings through a touch screen 124. Similar to the techniques described above with respect FIGS. 4 and 5, the touch screen 124 may be used to adjust the alarm settings and view how the changed settings affect the alarm conditions. Further, as described below, the touch screen may be used to adjust certain alarm conditions to determine alarm settings. For example, through the touch screen 124, a user may select portions of the representative pleth waveform 96 that the user would like to produce alarms. Based on the selections, the alarm modeling feature 80 and/or 92 may determine the alarm settings that may produce the user selected alarms.

The touch screen 124 may be included with the display 18 of the patient monitor 10 and/or with the display 66 of the central station 64. A screen 125 may be displayed on the touch screen 124 and may include the representative waveform 96, as well as the highlighted sections 104. Further, the touch screen 124 may display selectable graphical elements 126 and 128 that may be selected by a user to enable or disable alarm events for the highlighted sections 104. The graphical elements 126 and 128 may be selected by a user to toggle the status of the graphical elements 126 and 128 between an alarm status and a no alarm status. For example, as shown in FIG. 7, user may select the graphical element 126 within the highlighted section 104a to change the alarm condition from the currently shown alarm setting to a no alarm setting. A user may select the graphical element 128 within the highlighted section 104b to disable the alarm for that section of physiological data. A user may select the graphical element 126 shown in the highlighted section 104c to enable an alarm for the highlighted portion.

Upon selection of the graphical elements 126 and 128, a screen 132 may be displayed as shown in FIG. 8 to reflect the new alarm events. After a user has adjusted the alarm limits and selected the desired graphical elements 126 and 128, a user may select the graphical element 138 to determine the new alarm limit settings. The patient monitor 10 may then determine the new alarm limits and then display the new alarm limits on the screen 132 shown in FIG. 8. For example, as shown in the section of the screen 109, based on the selectable graphical elements, the patient monitor has adjusted the SatSeconds™ value from 100 to 125 and increased the SPD threshold from the mid level to the high level as shown by the label 40.

A user also may adjust the alarm limits by selecting the graphical elements 130 and 132 to display alarm adjustment menus as described above with respect to FIGS. 4 and 5. Moreover, as discussed above with respect to FIGS. 4 and 5, a user may select the graphical element 134 to change the representative pleth waveform 96 that is displayed and/or to change the timeframe for the representative pleth waveform 96.

Figure 9:
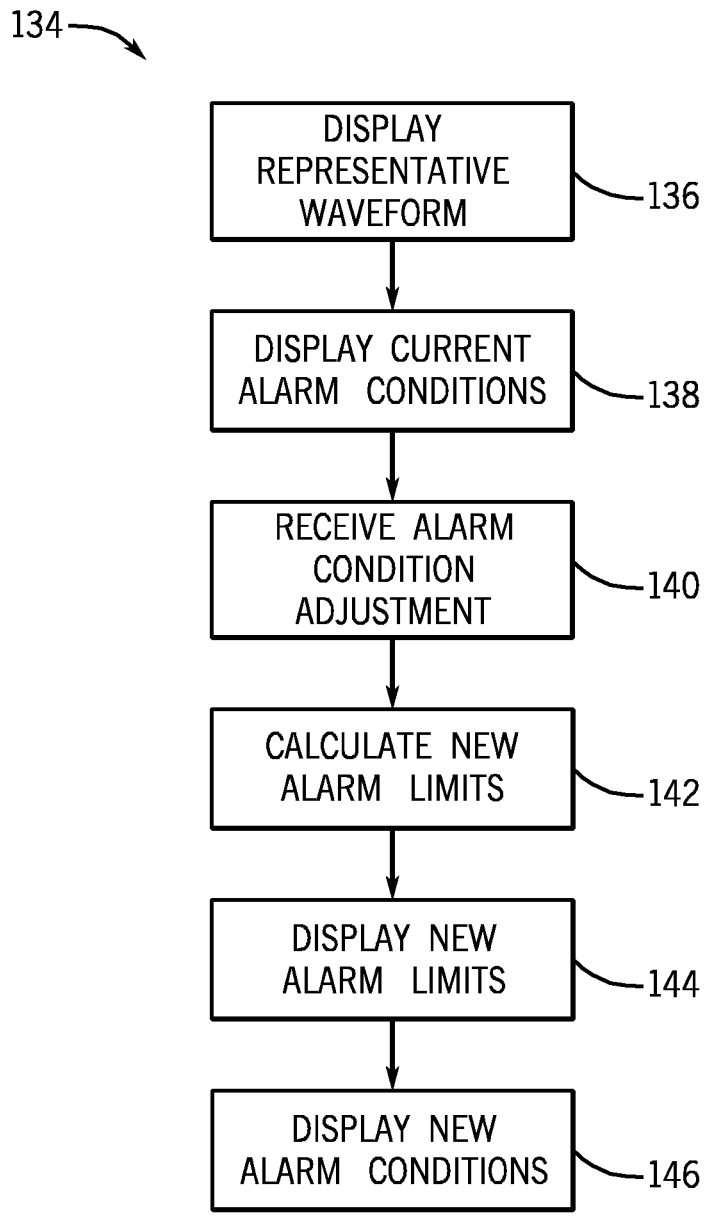
FIG. 9 is a flowchart of an embodiment of a method for setting alarm thresholds using an alarm modeling feature.

FIG. 9 shows an embodiment of a method 134 for determining alarm limits by setting sections 104 of the representative waveform to specific alarm conditions. The method 134 may begin by displaying (block 136) the representative pleth waveform. For example, the representative waveform 96 may be displayed on the patient monitor 10 or on the central station 64 as shown in FIGS. 7 and 8. The patient monitor 10 may then display (block 138) the current alarm conditions. For example, the current alarm conditions may be shown by the indicators 126 and 128 shown in FIG. 7 and may be calculated using the current alarm settings.

The patient monitor 10 may then receive (block 140) an alarm condition adjustment. For example, a user may select the graphical elements 126 and 128 to toggle the alarm conditions for sections 104 of the representative pleth waveform 96. Moreover, in certain embodiments, a user may adjust the alarm limits directly using the selectable inputs 16 (FIG. 1), the soft keys 54 (FIG. 1), and/or the graphical elements 130 and 132 (FIG. 7). The patient monitor 10 may then calculate (block 142) the new alarm limits based on the received alarm adjustments. For example, the microprocessors 32 and 86 of the patient monitor 10 and the central station 64 may compare the selected alarm conditions to alarm limit look up tables stored within the memories 78 and 90. Further, the processors 72 and 86 may apply calculation algorithms stored within the memories 78 and 90, for example, within the alarm modeling features 80 and 92, to determine the new alarm limits.

After the new alarm limits are calculated, the patient monitor 10 may display (block 144) the new alarm limits on the display 18 or 66. For example, the new alarm limits may be displayed within the labels 38 and 40 as shown in FIGS. 5 and 8. Moreover, the alarm limits 30 and 32 may also be updated to reflect the new oxygen saturation and/or pulse rate levels. The patient monitor may also display (block 146) the new alarm conditions. For example, as shown in FIG. 8, the new alarm limits may be shown by the graphical elements 126 and 128 within the highlighted sections 104 of the representative waveform 96.

In addition to, or instead of selecting graphical elements to enable or disable alarms for portions of the representative waveform 96, a user may adjust portions of the representative waveform 96 directly to set alarm limits. As shown in FIG. 10, a screen 148 may be shown on the touch screen 124. The screen 148 may include selection bars 152 that may be dragged by a user to manipulate the representative pleth waveform 96. For example, as shown in the highlighted section 104a that identifies a SatSeconds™ alarm condition, the selection bar 150 may be decreased in size to enable an alarm sooner using the SatSeconds™ alarm management feature. Similarly, the selection bar 152 may be decreased in size to decrease the SatSeconds™ value and alarm sooner when an oxygen desaturation event is detected.

Similarly, the highlighted section 104b that identifies an OxiMax SPD™ alarm condition may include the selection bar 150, which may be increased or decreased in size to correspond increase or decrease the SPD threshold value. A user also may highlight sections of the representative waveform to produce alarms on sections of the representative waveform 96 that previously did not alarm. For example, the desaturation event 153 currently is not highlighted as shown in FIG. 10. However, a user may select that area by highlighting a section to produce a highlighted section 104c as shown in FIG. 11. Adjustments using the selection bars 150 and 152 may increase or decrease the alarm limit settings. For example, as shown in FIG. 10, a user may decrease the magnitude of the desaturation event shown in highlighted section 104a and also may decrease the duration to alter the representative waveform 96 to create a desaturation event that alarms sooner and at a shallower desaturation depth.

After a user has made adjustments, the user may select the graphical element 138 to determine the new alarm limits. For example, a user may have adjusted the representative pleth waveform 96 shown in FIG. 10 to decrease the magnitude and duration of the saturation even shown in section 104a. A user also may have deselected the section 104b to indicate that no alarm should occur for section 104b. Further, a user may have selected the desaturation event 153 to indicate that an alarm should occur.

The changes to the representative pleth waveform 96 may be seen by comparing the screen 148 of FIG. 10 to a screen 154 shown in FIG. 11. For example, the highlighted section 104a has decreased in size, which may generally indicate that a SatSeconds™ alarm will occur at a lower threshold. Moreover, the highlighted section 104b has been omitted. For example, a user may have narrowed the selection bar 150 shown in FIG. 10 to eliminate the highlighted section 104b indicating that no alarm may occur for this portion of the representative waveform 96. As shown in FIG. 11, the desaturation event 153 has now been highlighted by a user to produce the highlighted section 104c, indicating that an alarm may now be produced for this portion of the representative waveform.

Based on the changed alarm conditions, the patient monitor 10 may determine and display the new alarm limit settings.

For example, a user may select the graphical element 138 to cause the patient monitor 10 to calculate new alarm limit settings corresponding to the changed alarm conditions. The patient monitor may determine and display the new alarm limits as generally described above with respect to FIG. 9. For example, the patient monitor 10 may display a reduced Sat-Seconds™ value of "25" in label 38 of screen 154. The patient monitor 10 also may display an increased OxiMax SPD™ threshold of "3" in label 40 of screen 154.

As may be appreciated, the screens described above with respect to FIGS. 4-10 may be employed with displays with or without touch screens. Furthermore, any combination of the indicators, adjustment techniques, labels, and the like may be employed. Moreover, the relative sizes, shapes, numbers, and geometries of the indicators and graphical elements may vary. For example, in certain embodiments, other types of graphical representations, such as plots, graphs, or charts, among others, may be employed instead of, or in addition to a representative pleth waveform.

What is claimed is:

1. A patient monitor, comprising:
   a medical device interface suitable for operable connection to a sensor;
   a display configured to display patient physiological data based on input received from the sensor and to display a graphical representation of representative physiological data;
   a graphical user interface configured to receive a user input that alters existing alarm limits for the patient physiological data; and
   an alarm modeling feature configured to analyze the representative physiological data to identify alarm conditions corresponding to the altered alarm limits and configured to display indicators that identify the alarm conditions associated with the altered alarm limits and that identify the alarm conditions associated with the previously existing alarm limits that no longer represent alarm conditions on the graphical representation.

2. The patient monitor of claim 1, wherein the patient physiological data and the representative physiological data comprise $SpO_2$ values and wherein the graphical representation comprises a plethysmographic waveform.

3. The patient monitor of claim 1, wherein the representative physiological data comprises a historical trend of the patient physiological data.

4. The patient monitor of claim 1, wherein the representative physiological data comprises sample physiological data included within the alarm modeling feature.

5. The patient monitor of claim 1, wherein the graphical user interface includes a screen configured to display the graphical representation, the existing alarm limits, and highlighted sections of the graphical representation identifying alarm events corresponding to the existing alarm limits.

6. The patient monitor of claim 1, wherein the display comprises a touch screen and wherein the indicators comprise touch sensitive graphical elements selectable by a user to alter the alarm limits.

7. The patient monitor of claim 1, wherein the alarm limits comprise $SpO_2$ limits, an oxygen saturation pattern detection threshold, or a value specifying a product of magnitude and duration of an oxygen desaturation event, or a combination thereof.

8. The patient monitor of claim 1, wherein the indicators comprise graphical elements selected by a user to adjust the alarm conditions for a corresponding portion of the graphical representation.

9. The patient monitor of claim 8, wherein the alarm model feature is configured to determine new alarm limits corresponding to the adjusted alarm conditions.

10. A patient monitoring system, comprising: one or more patient monitors; a central monitoring station coupled to the patient monitors and comprising:
    a display configured to display a graphical representation simulating patient physiological data received from the patient monitors; and a graphical user interface comprising alarm indicators configured to be displayed with the graphical representation to indicate alarm conditions for portions of the graphical representation, wherein each alarm indicator is displayed adjacent a specific portion of the graphical representation where a respective alarm condition occurs; an alarm modeling feature configured to modify the display of the alarm indicators in response to a user input altering alarm limits for the patient physiological data and configured to display indicators that identify the alarm conditions associated with the altered alarm limits and that identify the alarm conditions associated with the previously existing alarm limits that no longer represent alarm conditions on the graphical representation.

11. The patient monitoring system of claim 10, wherein the display is configured to display the patient physiological data received from each of the patient monitors.

12. The patient monitoring system of claim 10, wherein the graphical representation comprises a historical trend of patient physiological data received from one of the patient monitors.

13. The patient monitoring system of claim 10, wherein the central monitoring station comprises a communication interface configured to apply the altered alarm limits to the patient monitors.

14. The patient monitoring system of claim 10, wherein the central monitoring station comprises a touch screen for receiving the user input.

15. A method, comprising:
    displaying a graphical representation of patient physiological data;
    displaying indicators identifying current alarm events corresponding to sections of the graphical representation based on current alarm limits, wherein each indicator is displayed adjacent a specific section of the graphical representation where a respective current alarm event occurs;
    receiving a user input adjusting alarm limits used to determine the current alarm events;
    determining new alarm events based on the adjusted alarm limits; and
    displaying indicators that identify the alarm conditions associated with the altered alarm limits and identify the alarm conditions associated with the previously existing alarm limits that no longer represent alarm conditions on the graphical representation.

16. The method of claim 15, wherein displaying the graphical representation comprises selecting a plethysmographic waveform from a plurality of stored plethysmographic waveforms based on the alarm limits.

17. The method of claim 15, wherein receiving a user input comprises receiving a user input altering a shape of the graphical representation and determining adjusted alarm limits based on the altered shape.

18. The method of claim 15, wherein receiving a user input comprises receiving a user input highlighting one or more portions of the graphical representation where alarms should occur.

19. The method of claim 15, wherein altering the display of the indicators comprises toggling the indicators between an alarm status and a no alarm status.

20. The method of claim 15, comprising applying the adjusted alarm limits to one or more patient monitors.

* * * * *